United States Patent [19]

Gruber

[11] Patent Number: 4,720,575

[45] Date of Patent: Jan. 19, 1988

[54] $H_8PMO_{10}VO_{39}$ AND ITS ANHYDRIDE, $PMO_{10}VO_{35}$ AND PREPARATION THEREWITH OF METHACRYLIC ACID AND ITS LOWER ALKYL ESTER

[75] Inventor: Wilhelm Gruber, Darmstadt, Fed. Rep. of Germany

[73] Assignee: Röhm GmbH, Darmstadt, Fed. Rep. of Germany

[21] Appl. No.: 837,529

[22] Filed: Mar. 7, 1986

[30] Foreign Application Priority Data

Mar. 12, 1985 [DE] Fed. Rep. of Germany ....... 3508649

[51] Int. Cl.$^4$ .............................................. C07C 67/30
[52] U.S. Cl. ..................................... 560/214; 423/306; 502/209; 562/535; 562/538; 562/549; 562/599
[58] Field of Search ............... 562/547, 599, 535, 538, 562/549; 560/214; 423/306; 502/209

[56] References Cited

U.S. PATENT DOCUMENTS 4,146,574  3/1979  Okada et al. .................... 423/299
4,192,951  3/1980  Slinkard et al. ................. 562/547

FOREIGN PATENT DOCUMENTS 1523849   9/1978  United Kingdom ............... 562/599
2046252  11/1980  United Kingdom ............... 562/534

*Primary Examiner*—Werren B. Lone
*Attorney, Agent, or Firm*—Curtis, Morris & Safford

[57] ABSTRACT

The molybdovanadophosphoric acid $H_8PMo_{10}VO_{39}$, its $PMo_{10}VO_{35}$ anhydride, methods for their preparation, and methods for making methacrylic acid and its esters by oxidation/dehydrogenation wherein the above acid and/or its anhydride is employed as a catalyst.

6 Claims, No Drawings

$H_8PMo_{10}VO_{39}$ AND ITS ANHYDRIDE, $PMo_{10}VO_{35}$ AND PREPARATION THEREWITH OF METHACRYLIC ACID AND ITS LOWER ALKYL ESTER

The present invention relates to a heteropolyacid having phosphorus as the central atom and molybdenum and vanadium as peripheral atoms in the anion, to the anhydride of such an acid, to methods for making the acid and anhydride, and to methods for effecting organic reactions in the presence of the acid or anhydride as a catalyst.

A classification of the heteropolyacid of molybdenum and tungsten by G. A. Tsigdinos, Topics in Current Chemistry, 76 (1978), 1–64, shows that this class of compounds includes compounds having widely differing elements as central atoms, in different atomic ratios and with different crystal structures, some of which are still unknown. One of these series, the 12-heteropolyacids of the general formula $$H^{(8-n)}[X^{n+}Mo_{12}(W)_{12}O_{40}],$$

where X is the central atom, includes the molybdenum and tungsten heteropolyacids $H_3PMo_{12}O_{40}.30\ H_2O$ and $H_3PW_{12}O_{40}.29H_2O$, which are among the earliest known and extensively investigated heteropolyacids. Another series of heteropolyacid compounds is characterized by the anion $[X^{n+}Mo_{11}O_{39}]^{-(12-n)}$, where $P^{5+}$, $As^{5+}$, and $Ge^{4+}$ may be the central atom X, of which series at present only the 11-molybdo-germanate anion is definitely known. Its crystal structure is still unknown and is not identical with that of the aforesaid 12-heteropolyacids, the Keggin structure, named after its discoverer.

12-molybdophosphoric acid, $H_3PMo_{12}O_{40}$, and its vanadium derivatives, that is the molybdovanadophosphoric acids $H_{3+x}PMo_{12-x}V_xO_{40}$, are known as heteropolyacid catalysts for effecting selective oxidations and also for the oxidative dehydrogenation of isobutyric acid or its esters to methacrylic acid or its esters. In Studies in Surfactant Science and Catalysis, 7 (1981), 780–791, it is shown that the partial replacement of molybdenum by vanadium to give $H_5PMo_{10}V_2O_{40}$ will increase the selectivity for methacrylic acid of the $H_3PMo_{12}O_{40}$ catalyst from 40 to 73 percent with nearly constant isobutyric acid conversion.

The preparation of the $H_4PMo_{11}VO_{40}$, $H_5PMo_{10}V_2O_{40}$, and $H_6PMo_9V_3O_{40}$ molybdovanadophosphoric acids has been described by Tsigdinos and Fallada in Inorg. Chem. 7 (1968), 437–441, and a further process which, in contrast to the first-mentioned process, is based not on salts of the starting compounds but on the oxides or the free acids such as $MoO_3$, $V_2O_5$, and $H_3PO_4$, is disclosed in published German patent application No. DOS 27 22 375. The Examples describe practically only the preparation of the $H_5PMo_{10}V_2O_{40}$ heteropolyacid, which is then used to produce oxidation catalysts with which various oxidation reactions, including the oxidative dehydrogenation of isobutyric acid and its methyl esters, are carried out.

Published German patent application No. DOS 30 10 434 describes a process for the preparation of methacrylic acid by the oxidation of methacrolein which proceeds in the presence of catalysts of the general formula $Mo_aV_bP_cX_dY_eO_f$, where X represents one or more elements selected from the group consisting of copper, tin, thorium, germanium, nickel, iron, cobalt, zinc, titanium, lead, aluminum, zirconium, cerium, bismuth, and arsenic, Y represents one or more elements from the group consisting of potassium, rubidium, cesium, and thallium, and a, b, c, d, e, and f represent the atomic ratios. In that German patent application, these catalysts are referred to as catalysts having a heteropolyacid salt structure. An example of such a catalyst is the product having the composition $Mo_{10}V_1P_1Cu_{0.2}$ and the equivalent amount of oxygen.

Published German patent application No. DOS 32 48 600 states that Mo-V-Cu-P catalysts, for example catalysts with $Cu_{0.2}PMo_{10}VO_{35.2}$, accelerate the oxidative dehydrogenation of isobutyric acid to methacrylic acid in high selectivities of up to 82.7 percent. However, these catalysts have the serious drawback that they are deactivated rather quickly so that from the commercial point of view their service life is too short.

The temperature range for carrying out the oxidative dehydrogenation of isobutyric acid or its esters with heteropolyacid catalysts is 250° C. to 500° C., and preferably 300° C. to 400° C. By means of infrared spectroscopy, it was determined on $H_5PMo_{10}V_2O_{40}$ catalyst samples, from the occurrence of $MoO_3$ spectral bands, that the "heteropolyacid association" here present clearly dissociates into its oxidic constituents at 375° C. This thermal decomposition in the temperature region of importance to oxidative dehydrogenation is a principal factor in the steady decline of the activities of $H_5PMo_{10}V_2O_{40}$ and $Cu_{0.2}PMo_{10}VO_{35.2}$ catalysts.

Thus, it was necessary to seek a more thermally stable heteropolyacid containing the elements phosphorus, molybdenum, and vanadium that is also suitable for use as a catalyst in chemical reactions.

Surprisingly, it has been found that by the reaction of molybdenum trioxide and vanadium pentoxide in aqueous phosphoric acid in a molar ratio of 10:0.5:1 according to the hydrothermal conversion process described in published German patent application No. DOS 27 22 375 a new heteropolyacid, 10-molybdovanadophosphoric acid, having the formula $$H_8PMo_{10}VO_{39},$$

is formed in a practically quantitative yield. It is a species of the little-known $[X^{b+}Mo_{11}O_{39}]^{-(12-n)}$ series mentioned earlier, with $P^{5+}$ as the central atom $X^{n+}$ and with the substitution of a Mo atom by a V atom, which results in the eightfold negative change on the $PMo_{10}VO_{39}$ anion. From the new heteropolyacid, its anhydride, the new compound $PMo_{10}VO_{35}$, can be prepared by dehydration.

It has further been found that the new heteropolyacid and its anhydride possess good catalytic properties, especially in oxidation/dehydrogenation processes. Thus, it has been found, for example, that the drawback of the known processes for the oxidative dehydrogenation of isobutyric acid to methacrylic acid, namely the rapid deactivation of the catalyst, is overcome by catalysts made from the new molybdovanadophosphoric acid.

The present invention thus relates particularly to the new heteropolyacid $H_8PMo_{10}VO_{39}$, to its anhydride $PMo_{10}VO_{35}$, to methods for their preparation, and to the use of the new substances as catalysts.

The new compound is obtained in orange colored crystals by crystallization from an aqueous medium as a compound containing approximately 25 to 35 moles of water of crystallization, usually as $$H_8PMo_{10}VO_{39} \cdot 32H_2O,$$

in very pure form.

Its thermal behavior may be represented by the following scheme:

$$H_8PMo_{10}VO_{39} \cdot 32H_2O \xrightarrow[-32H_2O]{100°\text{ C.}-200°\text{ C.}} H_8PMo_{10}VO_{39}$$

$$H_8PMo_{10}VO_{39} \xrightarrow[-4H_2O]{200°\text{ C.}-400°\text{ C.}} PMo_{10}VO_{35}$$

$$PMo_{10}VO_{35} \xrightarrow{\text{from about 425° C.}} MoO_3 + \ldots$$

The orange colored compound containing water of crystallization assumes, afer liberation of the latter, an orange-brownish hue which upon further liberation of the water of constitution turns ocher by the formation of $PMo_{10}VO_{35}$. By treatment with water, the heteropolyacid can be reconstituted from the anhydride. Infrared investigations of heated samples show that the P-Mo-V-O association of the $H_8PMo_{10}V_{39}$ heteropolyacid or its anhydride possesses markedly higher thermal stability than that of the $H_5PMo_{10}V_2O_{40}$ heteropolyacid.

|  | Decomposition sets in at about | Complete MoO₃ spectrum up to |
|---|---|---|
| $H_5PMo_{10}V_2O_{40}$ | 375° C. | 400° C. |
| $H_8PMo_{10}V_{39}$ | 425° C. | 450° C. |

In $^{31}P$ nuclear magnetic resonance investigations, $H_8PMo_{10}VO_{39}$ has been shown only one signal, at $\delta = -3.35$ ppm, with $H_3PO_4$ as an external standard, whereas in the investigation even of repeatedly recrystallized $H_5PMo_{10}V_2O_{40}$ several signals, with $\delta = -3.89$, $-3.62$, and $-3.53$ ppm occur. These results show that the new heteropolyacid is obtained in pure form and confirm the statements of both Tsigdinos and Fallada, Inorg. Chem. 7 (1968), 437–441, and Spitsyn et al., Sov. Sci. Rev., sect. B, 1981, 3, pp. 135–140, to the effect that $H_5PMo_{10}V_2O_{40}$ can be both a mixture of isomeric compounds and can be contaminated with the heteropoly acids $H_4PMo_{11}VO_{40}$ and $H_6PMo_9V_3O_{40}$. According to Spitsyn et al., only the NMR method makes it possible to demonstrate the individuality of the heteropolyacid anion.

As a typical heteropolyacid, $H_8PMo_{10}VO_{39}$ has strongly acidic and oxidizing properties. As an oxidizing agent, it is reduced but can readily be reoxidized. Because of these distinct properties, the new heteropolyacid and the anhydride which may be prepared from it lend themselves extremely well to use as catalysts in many reactions, by both homogeneous and heterogeneous procedures. Their acidic properties yield catalysts for esterifications, for example, or for additions of compounds having active hydrogen atoms to multiple bond systems, such as the addition of H₂O or of alcohols to olefins. Because of their oxidizing properties and their rapid reoxidation, $H_8PMo_{10}VO_{39}$ and $PMo_{10}VO_{35}$ can be used as catalysts in both homogeneous and heterogeneous phase in oxidations, dehydrogenations, and oxidative dehydrogenations. Examples of such reactions are the oxidation of olefins such as propylene or isobutylene, or of isobutane or tert.-butanol, to the corresponding aldehydes and their further oxidation to the unsaturated acids, for example acrylic acid or methacrylic acid. Similarly, methacrolein can be oxidized to methacrylic acid. Further examples are the oxidative dehydrogenation of ethylbenzene to styrene, or of isobutyraldehyde, isobutyric acid, or its esters, to methacrylic acid or its esters. Ammoxidation to saturated or unsaturated nitriles and the production of maleic anhydride from benzene or C₄-hydrocarbons are also catalyzed by the new heteropolyacid or its anhydride.

The catalyzed syntheses of methacrylic acid and its esters from compounds of the formula $$H_2C-\underset{\underset{R}{|}}{\overset{\overset{CH_3}{|}}{C}}-\underset{\underset{Y}{|}}{\overset{\overset{X}{|}}{C}}-Z,$$

wherein
R is H,
R' is H or OH, and
X, Y, and Z are all H; or
R and R' are H,
X and Y taken together are =O, and
Z is H, OH, or OR" where R" is (C₁-C₄)-alkyl; or
R and R' taken together with the carbon atoms to which they are attached from a C=C bond and X, Y, and X are all H; or
R and R' taken together with the carbon atoms to which they are attached form a C=C bond,
X and Y taken together are O, and
Z is H,
are of particular importance.

A further potential use of the new heteropolyacid is in the production of dyes.

Tests run with catalysts prepared from the new heteropolyacid have shown that the catalysts are active and selective for oxidative dehydrogenation reactions. The highest selectivities for methacrylic acid obtained so far with catalysts prepared from the new heteropolyacid are about 76 percent. Thus, they are practically as high as those obtained with catalysts prepared from $H_5PMo_{10}V_2O_{40}$ and just a few percentage points lower than those obtained by the process described in published German patent application No. DOS 32 48 600. However, it has further been found that because of the characteristic thermal properties of the $H_8PMo_{10}VO_{39}$ heteropolyacid, the new catalysts also possess higher thermal stability than the heteropolyacid and heteropolyacid salt catalysts known up to now and therefore have a considerably longer service life in oxidative dehydrogenation reactions. In the Examples given in the prior art, the reaction temperatures reported as measured in the reactors are lower, for example, than the temperature of 375° C. given earlier for the incipient decomposition of the $H_5PMO_{10}V_2O_{40}$ heteropolyacid. However, such reaction temperature data are macroscopic measures that reveal nothing about the temperatures actually prevailing at the site of the catalytic oxidation. There, as is known, excessively high temperatures may prevail, and these may develop into measurable "hot spots". When the excessively high temperatures and the "hot spots" reach a temperature range in which the catalytically active substances undergoes a phase change, its catalytic behavior may be altered. As is also true in the case of heteropolyacids, this is frequently accompanied by a decrease in service life, and hence, in productivity. It is therefore always advisable to maintain a sizable difference between the set reaction temperature and the phase-change temperature. This is readily accomplished with the new heteropolyacid, which is active and selective in oxidative dehydrogenation.

The new heteropolyacid of the invention is formed by the hydrothermal conversion process described in published German patent application No. DOS 27 22 375 for the production of molybdo- or tungsto-vanadophosphoric acids, that is by conversion of the oxides or oxyacids of $Mo^{6+}$, $V^{5+}$, and $P^{5+}$ in an aqueous phase at temperatures of 60° C. or higher during a reaction time of, usually, several hours. To form the $H_8PMo_{10}VO_{39}$ heteropolyacid, the starting compounds are used in such a ratio that a stoichiometry of P:Mo:V=1:10:1 is obtained, which in the case of the starting substances $H_3PO_4$, $MoO_3$, and $V_2O_5$, for example, means a stoichiometry of 1:10:0.5. The formation of the heteropolyacid proceeds particularly well at the boiling point at normal pressure and manifests itself in gradual red-orange coloration of the aqueous solution. In a closed vessel, the conversion may also be carried out at higher temperatures, for example in the range from 100° C. to 250° C., which permits the reaction time to be reduced considerably. In the course of the preparation, the concentration of the heteropolyacid in the aqueous solution may vary over a wide range, for example from 10 to 50 percent by weight. As the aqueous solution is concentrated, the compound is obtained by crystallization.

The compound $H_8PMo_{10}VO_{39}.32H_2O$, or the corresponding heteropolyacid which is more or less free of water of crystallization, or the anhydride of the formula $PMo_{10}VO_{35}$ obtainable by heating the heteropolyacid to a temperature on the order of 400° C., can be used to prepare catalysts by methods known in the art, e.g. by the procedure described on pages 5 and 6 of published German patent application No. DOS 32 48 600 for the production of Cu-containing Mo-V-P heteropolyacid catalysts. Suitably, the active materials are adsorbed from solution onto inert material, suitably a siliceous substrate such as silica gel and/or diatomaceous earth or silicon carbide oralumina. The carrier is then dried.

The new heterpolyacid can be processed further, especially after the addition of inert substances, to form granular catalysts, shell catalysts, impregnation or immersion catalysts with shaped carriers, and catalyst compacts. The catalysts are suitably calcined at an elevated temperature from about 150° C. to about 300° C., for 1–4 hours, suitably 3 hours, prior to use.

In accordance with the present invention, the catalyst so obtained is suitably used in the oxidative dehydrogenation of isobutyric acid to methacrylic acid, or of the corresponding lower alkyl esters, such as methyl isobutyrate, to the corresponding lower alkyl esters of methacrylic acid, such as methyl methacrylate, in the vapor phase at temperatures ranging from 250° C. to 500° C.*), and preferably from 300° C. to 380° C. The gas mixture used suitably contains from 1 to 5 moles of oxygen, usually in the form of air, per mole of isobutyric acid or its ester, from 1 to 8 moles, and preferably from 1 to 4 moles, of steam, and, optionally, further inert diluent gases such as $N_2$, CO, or $CO_2$, which may be a circulating gas mixture coming from the oxidative dehydrogenation process and which, together with the introduced atmospheric nitrogen, amount to from 10 to 20 moles of further inert gas.

*)especially from 250° C. to 400° C.

The process can be carried out in a recirculating reactor or in a tubular rector or in several reaction systems, which may be cascaded. For example, a recirculating reactor may be used for the preliminary conversion and a tubular reactor for the final conversion. In continuous operation, the catalyst can be loaded with approximately (1 to 20)$\times 10^{-2}$ moles of isobutyric acid or its esters per kilogram of catalyst charge and per minute. Conversions ranging from 80 to 90 percent of the isobutyric acid or ester used can be obtained with a recirculating reactor and conversions close to 100 percent with a tubular reactor.

A better understanding of the present invention and of its many advantages will be had by referring to the following specific examples, given by way of illustration.

EXAMPLES

Example 1

Preparation of decamolybdovanadophosphoric acid, ($H_8PMo_{10}VO_{39}.32H_2O$)

1439.5 g (10 moles) of $MoO_3$ and 90.95 g (0.5 mole) of $V_2O_5$ were suspended in a solution of 98 g (1 mole) of $H_3PO_4$ in 7550 g of deionized water and this mixture was then heated for 18 hours at 100° C. with stirring. After 6 hours, practically everything had dissolved to give an orange-red solution. The cooled solution was freed of a trace of undissolved matter by filtration and the approximately 18% aqueous heteropolyacid solution was then concentrated in a rotary evaporator to a heteropolyacid content of practically 50%.

A portion of this solution was crystallized and the orange colored crystals were recrystallized twice from water. Heating to 120° C. and to 150° C. resulted in a weight loss of the substances, from which weight loss the initial water content was determined to be 25.6 percent by weight. This corresponds to 32 moles of water of crystallization per mole of heteropolyacid of the composition $H_8PMo_{10}VO_{39}$, the latter based on a determination of Mo and V. The X-ray pattern of the compound containing water of crystallization, obtained with Cu K$\alpha$ radiation, is very similar to that of $H_5PMo_{10}V_2O_{40}.(30-35)H_2O$. By comparison, the compounds free of water of crystallization give X-ray patterns which in part have markedly different $2\theta$ values.

| $H_8PMo_{10}VO_{39}$ (MW = 1673.49) | | | |
|---|---|---|---|
| Calculated: | Mo 57.34% | Found: | Mo 57.6% |
| | V 3.05% | | V 3.05% |

$^{31}$P NMR: $\delta$=3.35 ppm, measured as an approximately 50% aqueous solution at 80.98 MHz with $H_3PO_4$ as an external standard.

Example 2

Preparation of $PMo_{10}VO_{35}$ 100 g of the compound $H_8PMo_{10}VO_{39}$, free of water of crystallization, were heated to constant weight by raising the temperature from 200° C. to 300° C. This entailed a weight loss of 4.28 g, which corresponds to 4 moles of water, from the starting heteropolyacid. Determination of the Mo and V in the other colored residue showed that a $PMo_{10}VO_{35}$ compound was present and the heteropolyacid had become an anhydride by giving up its water of constitution.

| $PMo_{10}VO_{35}$ (MW = 1601.43) | | | |
|---|---|---|---|
| Calculated: | Mo 59.92% | Found: | Mo 59.9% |
| | V 3.18% | | V 3.2% |

Example 3

Granular catalyst with 70% $H_8PMo_{10}VO_{39}$ and 30% $SiO_2$ 18 g of diatomaceous earth and 3.5 g of powdered silica gel ("Aerosil 200") were added to 100 g of a 50% $H_8PMo_{10}VO_{39}$ solution. The entire mixture was evaporated to dryness and then dried for 6 hours at 120° C. Then the mass was reduced in size to orange colored 5 mm granules. Before being used as catalyst, these were calcined for 3 hours at 300° C.

OXIDATIVE DEHYDROGENATION OF ISOBUTYRIC ACID TO METHACRYLIC ACID

Example 4

Catalysis in a recirculating reactor with a catalyst according to Example 3

A vaporous mixture of 67.4 g of isobutyric acid, 133 liters of air (measured at 20° C.), and 262 liters of nitrogen (measured at 20° C.), corresponding to a molar ratio of isobutyric acid:oxygen:nitrogen of 1:1.5:20, was conducted per hour over 107.1 g (130 ml) of the catalyst prepared according to Example 3. The reaction temperature ranged from 324° C. to 330° C. The results obtained after two different reaction times are presented below.

| Reaction time (hours) | Isobutyric acid conversion (%) | Selectivity for methacrylic acid (%) | Space-time yield methacrylic acid (g/l/h) |
|---|---|---|---|
| 27.5 | 80.2 | 74.2 | 301.3 |
| 50 | 79.8 | 75.1 | 303.3 |

Example 5

A vaporous mixture of 67.4 g of isobutyric acid, 266 liters of air (measured at 20° C.), and 130 liters of nitrogen (measured at 20° C.), corresponding to a molar ratio of isobutyric acid:oxygen:nitrogen of 1:3:18.5, was conducted per hour in a recirculating reactor over 107 g (130 ml) of granules, ranging in size from 2 to 5 mm, prepared as in Example 3 from $H_3PMo_{10}VO_{39}$ and containing 70 percent by weight of $PMo_{10}VO_{35}$ and 30 percent by weight of $SiO_2$ (diatomaceous earth and silica gel in a ratio of 5:1), which had been calcined for 3 hours at 300° C. The reaction temperature ranged from 325° C. to 330° C. The test, which extended over 426 hours, showed that the activity and the selectivity remained constant for the entire duration of the test. The isobutyric acid conversions obtained under the conditions indicated were a practically constant 82 to 83%, with selectivities for methacrylic acid of about 72%.

Examples 6 and 7 and Comparison Examples 1 and 2

Comparison of catalysts prepared from $H_8PMo_{10}VO_{39}$ and $H_5PMo_{10}V_2O_{40}$, respectively, each containing 30% $SiO_2$ (diatomaceous earth/silica gel, ratio 5:1), calcined for 3 hours at 400° C.; tests run in a tubular reactor A vaporous mixture of isobutyric acid, water, and oxygen (as air) in a molar ratio of 1:2:1.5 was conducted over 2 ml of catalyst (particle size, 0.75 to 1 mm) in each case with a dwell time of 0.3 second and a reaction temperature of 350° C. The catalyst had been pretreated by drying for 3 hours at 200° C. in a drying oven in an air atmosphere, after which the samples were calcined for 3 hours in a salt bath at 400° C. while in an air or nitrogen stream (6 liters of air or nitrogen per hour in each case).

The results obtained are presented below as a function of the composition of the catalytic material and of the pretreatment of the catalyst.

| Example No. | Catalyst prepared from | Calcining atmosphere | Isobutyric acid conversion | Selectivity for methacrylic acid |
|---|---|---|---|---|
| 6 | $H_8PMo_{10}VO_{39}$ | Nitrogen | 97.5 | 63.3 |
| 7 | $H_8PMo_{10}VO_{39}$ | Air | 95.9 | 61.6 |
| Comparison Example 1 | | | | |
| | $H_5PMo_{10}V_2O_{40}$ | Nitrogen | 75.8 | 48.4 |
| Comparison Example 2 | | | | |
| | $H_5PMo_{10}V_2O_{40}$ | Air | 63.1 | 34.2 |

Under otherwise identical testing conditions, but after preheating at only 300° C., the catalysts* of comparison Examples 1 and 2 initially yield isobutyric acid conversions of 95%, with selectivities for methacrylic acid ranging from 65 to 70%. Hence, the comparison with Examples 6 and 7 shows that pretreatment at 400° C. causes thermal instability in the prior art catalysts, resulting in sharply decreased conversion and selectivity.
*of Examples 6 and 7 and

Example 8 and Comparative Example 3

An isobutyric acid/oxygen/nitrogen mixture (molar ratio 1:1:5.20) was conducted at 330° C. over 130 ml of catalyst in a recirculating reactor with a dwell time of 0.6 second.

The rapid loss of activity of the very selective $Cu_{0.2}PMo_{10}VO_{35.2}$ catalyst described in published German patent application No. DOS 32 48 600, in comparison with a catalyst in accordance with the invention, is apparent from a comparison of the results of Example 8 which follows with those of comparative Example 3.

| Example No. | Catalyst with 30% $SiO_2$ prepared from | Time (hours) | Isobutyric acid conversion (%) | Selectivity for methacrylic acid (%) |
|---|---|---|---|---|
| 8 | $H_8PMo_{10}VO_{39}$ | 30 | 80.1 | 73.8 |
| | | 70 | 79.7 | 73.8 |
| | | 184 | 79.9 | 73.7 |
| Comparative Example 3 | | | | |
| | $Cu_{0.2}PMo_{10}VO_{35.2}$ | 15 | 79.6 | 79.8 |
| | | 70 | 72.8 | 79.1 |
| | | 140 | 60 | 79.1 |

Example 9

Spherical catalyst carriers 8 mm in diameter, consisting of 93.1 percent by weight of $Al_2O_3$ and 5.6 percent by weight of $SiO_2$, having an internal surface area from 0.3 to 0.37 $m^2/g$ and an apparent porosity of from 55 to 60 percent, were heated to 100° C. in an approximately 70% aqueous $H_8PMo_{10}VO_{39}$ solution. The mixture was then allowed to cool gradually and then was separated from the excess solution by filtration. The beads, impregnated with catalytic material, were dried for 1 hour at 110° C. and then for 3 hours at 150° C. The $H_8PMo_{10}VO_{39}$ content of the catalyst was 33.7%.

A vaporous mixture of isobutyric acid and oxygen (as air) in a molar ratio of 1:1:5 was conducted at 340° C. over 169.9 g (130 ml) of the orange colored bead catalyst in a recirculating reactor with a loading of the pure catalyst mass of 2.364 $(10^{-4})$ mole of isobutyric acid per gram of catalytic mass and per minute. Under these conditions, an isobutyric acid conversion of 70.2% and a selectivity of methacrylic acid of 76% were obtained. The space-time yield of methacrylic acid was 287 grams/liter/hour.

Example 10

Spherical catalyst carriers 5 mm in diameter, consisting of 65.8 percent by weight of SiC, 28.5 percent by weight of $SiO_2$, and 4.7 percent of $Al_2O_3$, having an internal surface area from 0.01 to 0.3 $m^2/g$ and an apparent porosity from 43 to 48 percent, were impregnated with $H_8PMo_{10}VO_{39}$ as described in Example 9. The $H_8PMo_{10}VO_{39}$ content of the dried catalyst was 27.2%.

A vaporous mixture of isobutyric acid and oxygen (as air) in a molar ratio of 1:1.5 was conducted at 320° C. over 166.8 g (130 ml) of the orange-brown catalyst in a recirculating reactor with a loading of the pure catalyst mass of 4.729 $(10^{-4})$ mole isobutyric acid per gram of catalytic mass and per minute. The isobutyric acid conversion was 79.1%, the selectivity for methacrylic acid 70%, and the space-time yield 470 g of methacrylic acid/liter/hour.

What is claimed is:

1. A heteropolyacid of the formula $H_8PMo_{10}VO_{39}$.
2. The heteropolyacid $H_8PMo_{10}VO_{39}.32H_2O$.
3. The heteropolyacid anhydride $PMo_{10}VO_{35}$.
4. A heteropolyacid of the formula $H_8PMo_{10}VO_{39}.25-35H_2O$.
5. The method for making methacrylic acid or a lower ester thereof which comprises reacting a compound of the formula

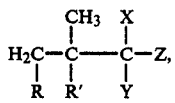

wherein
R is H,
R' is H or OH, and
X, Y, and Z are all H; or
R and R' are H,
X and Y taken together are =O, and
Z is H, OH, or OR" where R" is $(C_1-C_4)$-alkyl; or
R and R' taken together with the carbon atoms to which they are attached form a C=C bond and X, Y, and Z are all H; or
R and R' taken together with the carbon atoms to which they are attached form a C=C bond,
X and Y taken together are =O, and
Z is H, in the vapor phase in the presence of oxygen, at a temperature from 250° C. to 500° C., and in the presence of decamolybdovanadophosphoric acid, $H_8PMo_{10}VO_{39}$, and/or its anhydride, $PMo_{10}VO_{35}$, as a catalyst.

6. A method as in claim 5 wherein said catalyst is present in admixture with a carrier therefor.

* * * * *